US007049423B2

(12) United States Patent
Ryan

(10) Patent No.: US 7,049,423 B2
(45) Date of Patent: May 23, 2006

(54) **USE OF THE RTX SECRETION SYSTEM TO ACHIEVE HETEROLOGOUS POLYPEPTIDE SECRETION BY *VIBRIO CHOLERAE***

(75) Inventor: Edward T. Ryan, Wellesley, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 11/018,169

(22) Filed: Dec. 20, 2004

(65) Prior Publication Data

US 2005/0176106 A1 Aug. 11, 2005

Related U.S. Application Data

(60) Provisional application No. 60/531,282, filed on Dec. 19, 2003.

(51) Int. Cl.
*C07H 21/04* (2006.01)
*C12P 21/04* (2006.01)
*A61K 38/00* (2006.01)

(52) U.S. Cl. .................... 536/23.4; 435/69.7; 530/350

(58) Field of Classification Search .............. 536/23.4; 435/69.7; 530/350
See application file for complete search history.

(56) References Cited

U.S. PATENT DOCUMENTS 4,882,278 A 11/1989 Mekalanos .............. 435/172.3

OTHER PUBLICATIONS

Allo et al., "Prevention of Clindamycin-Induced Colitis in Hamsters by . . . " Gastroenterology 76(2):351-355, 1979.
Butterton et al., "Heterologous Antigen Expression in *Vibrio cholerae* Vector Strains" Infection and Immunity 63(7):2689-2696, 1995.
Bulletin of the World Health Organization, U.S. Institute of Med. Washington, D.C., National Academy Press, vol. 68(3):303-312, 1990.
Corthier et al., "Protection against Experimental Pseudomembranous Colitis in Gnotobiotic . . . " Infection and Immunity 59(3):1192-1195, 1991.
Dillon et al., "Involvement of Ras-Related Rho Proteins in the Mechanisms of . . . " Infection and Immunity 63(4):1421-1426, 1995.
Dove et al., "Molecular Characterization of the *Clostridium difficile* Toxin A Gene" Infection and Immunity 58(2):480-488, 1990.
Fullner et al., "*Vibrio cholerae*-Induced Cellular Responses of Polarized T84 . . . " Infection and Immunity 69(10):6310-6317, 2001.
Fullner et al., "In vivo covalent cross-linking of cellular actin by the *Vibrio cholerae* RTX toxin" The EMBO Journal 19(20):5315-5323, 2000.
Gentschev et al., "*Salmonella* Strain Secreting Active Listeriolysin Changes . . . " Infection and Immunity 63(10):4202-4205, 1995.
Herrington et al., "Toxin, Toxin-Coregulated Pili, and the *toxR* Regulon . . . " J. Exp. Med. 168:1487-1492, 1988.
Kelly et al., "Human Colonic Aspirates Containing Immunoglobulin A Antibody . . . " Gastroenterology 102:35-40, 1992.
Ketley et al., "The effects of *Clostridium difficile* crude toxins and toxin A . . . " J. Med. Microbiol. 24:41-52, 1987.
Kim et al., "Immunization of Adult Hamsters against *Clostridium difficile*-Associated . . . " Infection and Immunity 55(12):2984-2992, 1987.
Johnson et al., "Neutralization of a Bacterial Enterotoxin by Systemic IGA . . . " J. Immunol. 150:117A Abstract #657, 1993.
Krivan et al., "Cell Surface Binding Site for *Clostridium difficile* Enterotoxin: . . . " Infection and Immunity 53(3):573-581, 1986.
Leung et al., "Treatment with Intravenously Administered Gamma Globulin . . . " J. of Pediatrics 118(4):633-637, 1991.
Levine et al., "New Knowledge on Pathogenesis of Bacterial Enteric Infections . . . " Microbiological Rev. 47(4):510-550, 1983.
Levine et al., "Duration of Infection-Derived Immunity to Cholera" J. of Infectious Diseases 143(6):818-820, 1981.
Lin et al., "Identification of a *Vibrio cholerae* RTX toxin gene cluster that is . . . " Proc. Nat'l. Acad. Sci. USA 96:1071-1076, 1999.
Lyerly et al., "*Clostridium difficile*: Its Disease and Toxins" Clin. Microbiol. Rev. 1(1):1-18, 1988.
Mekalanos et al., "Cholera toxin genes: nucleotide sequence, deletion analysis . . . " Nature 306(5943):551-557, 1983.
Mitty et al., "*Clostridium difficile* Diarrhea: Pathogensis, Epidemiology, and Treatment" The Gastroenterologist 2(1):61-69, 1994.
Saroso et al.; "A controlled field trial of plain and aluminium hydroxide-adsorbed cholera . . . " Bulletin of the WHO 56(4):619-627, 1978.
Sauerborn et al., "Nucleotide Sequence of *Clostridium difficile* Toxin A" Nucleic Acids Res. 18(6):1629-1630, 1990.
Swerdlow et al., "Cholera in the Americas" JAMA 267(11):1495-1499, 1992.
Tauxe et al., "Epidemic Cholera in Latin America" JAMA 267(10):1388-1390, 1992.

(Continued)

*Primary Examiner*—Robert A. Wax
*Assistant Examiner*—Suzanne M. Mayer
(74) *Attorney, Agent, or Firm*—Fish & Richardson P.C.

(57) ABSTRACT

Compositions and methods for secreting large heterologous polypeptides are described.

23 Claims, 3 Drawing Sheets

OTHER PUBLICATIONS

Taylor et al., "Development of a Live, Oral, Attenuated Vaccine Against El Tor Cholera" J. of Infectious Diseases 170(6):1518-1523, 1994.

Tucker et al., "Toxin A of *Clostridium difficile* Binds to the Human Carbohydrate . . . " Infection and Immunity 59(1):73-78, 1991.

Von Eichel-Streiber et al., "*Clostridium difficile* toxin A carries a C-terminal repetitive . . . " Gene 96:107-113, 1990.

Warny et al., "Human Antibody Response to *Clostridium difficile* Toxin A . . . " Infection and Immunity 62(2):384-389, 1994.

Wren et al., "Antigenic Cross-Reactivity and Functional Inhibition by Antibodies . . . " Infection and Immunity 59(9):3151-3155, 1991.

USE OF THE RTX SECRETION SYSTEM TO ACHIEVE HETEROLOGOUS POLYPEPTIDE SECRETION BY *VIBRIO CHOLERAE*

RELATED APPLICATIONS

This application claims the benefit of U.S. Provisional Application No. 60/531,282 filed Dec. 19, 2003, the entire contents of which are hereby incorporated by reference herein.

BACKGROUND

*V. cholerae* is a gram-negative bacterium that, in its wild-type state, causes severe, dehydrating and occasionally fatal diarrhea in humans. There are an estimated 5.5 million cases of cholera each year, resulting in greater than 100,000 deaths (Bull. W.H.O. 68:303–312, 1990). Over the last several decades, cholera has been considered to occur primarily in developing countries of Asia and Africa, but recently it has reached epidemic proportions in regions of South and Central America as well (Tauxe et al., J. Am. Med. Assn. 267:1388–1390, 1992; Swerdlow et al., J. Am. Med. Assn. 267:1495–1499, 1992).

Patients who recover from cholera infection have long-lasting, perhaps lifelong, immunity to reinfection (Levine et al., J. Infect. Dis. 143:818–820, 1981). The development of *V. cholerae* vaccines has focused on reproducing this naturally occurring immunity, but the conventional, parenteral, killed whole-cell vaccine preparation provides less than 50% protection from disease, for a duration of only 3 to 6 months (Saroso et al., Bull. W.H.O. 56:619–627, 1978; Levine et al., Microbiol. Rev. 47:510–550, 1983).

The most important virulence factor for *V. cholerae* in causing clinical disease is cholera toxin, a protein complex consisting of one A subunit and five B subunits. An internal deletion of the gene encoding the A subunit of cholera toxin (ctxA) in the classical strain 0395 produces a strain (0395-N1) that is highly immunogenic in humans (Mekalanos, 1983, Nature 306:551–557; Herrington, 1988, J. Exp. Med. 168:1487–1492; Mekalanos, U.S. Pat. No. 4,882,278, herein incorporated by reference).

SUMMARY OF THE INVENTION

The invention is based, at least in part, on the discovery that the RTX secretion system of *Vibrio cholerae* can be used to express and secrete heterologous polypeptides, e.g., fusion proteins containing heterologous polypeptides. Accordingly, in one aspect, the invention features nucleic acids the encode fusion proteins, e.g., fusion proteins that contain (i) a fragment of a *V. cholerae* RTX protein that includes the RTX secretion signal sequence and (ii) a heterologous polypeptide, e.g., a heterologous antigen. The fragment of the RTX protein can include, e.g., at least 40, e.g., at least 50, 60, 70, 80, 90, 100, 105, 110, 125, or 150, carboxyl terminal amino acids of the RTX protein. In another embodiment, the fragment of the RTX protein can include, e.g., between 40 and 100 carboxyl terminal amino acids of the RTX protein. Preferably, the fragment includes 100 carboxyl terminal amino acids of the RTX protein. Preferably, the fragment includes 105 carboxyl terminal amino acids of the RTX protein.

In one embodiment, the nucleic acid encodes a fusion protein that further includes an amino terminal fragment of the RTX protein. The amino terminal fragment of the RTX protein can include, e.g., 1, 2, 3, 4, 5, 10, 15, 20, 30, 40 or 50 amino acids. In a preferred embodiment, the amino terminal fragment is 50 amino acids.

In one embodiment, the nucleic acid encodes a fusion protein wherein the heterologous polypeptide, e.g., the heterologous antigen, is located between the amino terminal fragment of the RTX protein and the carboxyl terminal fragment of the RTX protein.

In another embodiment, the nucleic acid encodes a fusion protein that contains a fragment of a *V. cholerae* RTX protein (e.g., a fragment that includes the RTX secretion signal sequence) and *C. difficile* toxin A, or an antigenic portion thereof. For example, the antigenic portion can be a carboxyl terminal fragment of *C. difficile* toxin A. The carboxyl terminal fragment can be, e.g., at least 100, 200, 300, 400, 500 or more, carboxyl terminal amino acids of *C. difficile* toxin A. Preferably, the carboxyl terminal fragment is 300 amino acids.

In another aspect, the invention features expression vectors, e.g., expression vectors that include a nucleic acid described herein.

In another aspect, the invention features *V. cholerae* cells that contain an expression vector described herein. For example, a *V. cholerae* cell can be transfected with an expression vector described herein and can express a fusion protein described herein. Preferably, the *V. cholerae* cell secretes the expressed fusion protein. For example, a *V. cholerae* cell maintained in culture can secrete a fusion protein described herein into the culture medium. Alternatively, a *V. cholerae* cell introduced into a host can secrete a fusion protein described herein into the host.

A *V. cholerae* cell can be an El Tor *V. cholerae* cell. The El Tor *V. cholerae* cell can be, e.g., a cell that does not express full-length cholera toxin A subunit. For example, the *V. cholerae* cell can be a Peru2 *V. cholerae* cell.

In another aspect, the invention features fusion proteins that include (i) a fragment of a *V. cholerae* RTX protein that includes the RTX secretion signal sequence and (ii) a heterologous polypeptide, e.g., a heterologous antigen. The fusion protein can be one that is encoded by a nucleic acid described herein.

In another aspect, the invention features methods for producing a fusion protein described herein. The method can include maintaining a cell, e.g., a *V. cholerae* cell described herein, under conditions sufficient to allow expression of the fusion protein.

In another aspect, the invention features methods of inducing an immune response in an animal. The method includes administering to an animal (e.g., a mammal, e.g., a human, non-human primate, cow, horse, sheep, goat, pig, dog, cat, rabbit, rat, mouse, guinea pig or hamster) a *V. cholerae* cell described herein, in an amount sufficient to elicit an immune response. The immune response can be a systemic response, i.e., mediated by an IgG antibody response, or a mucosal response, i.e., mediated by an IgA antibody response. The immune response can be directed against the RTX protein, the heterologous polypeptide, e.g., heterologous antigen, or both. Preferably, the immune response is induced against both the RTX protein and the heterologous polypeptide, as well as against other antigens expressed by the cell.

Definitions

As used herein, an "expression vector" is a nucleic acid construct, generated recombinantly or synthetically, that has control elements that are capable of affecting expression of a coding sequence that is "operably linked" to the control elements in hosts compatible with such sequences. Expression vectors typically include at least promoters and optionally transcription termination signals and polyadenylation signals. A coding sequence is operably linked to an expression control sequence when the expression control sequence controls and regulates the transcription and translation of that coding sequence. Expression requires having an appropriate start signal (e.g., ATG) in front of the coding sequence to be expressed and maintaining the correct reading frame to permit expression of the coding sequence under the control of the expression control sequence and production of the desired polypeptide encoded by the coding sequence.

The terms "peptide", "polypeptide" and "protein" are used interchangeably herein. The terms "nucleic acid" and "nucleotide sequence" are also used interchangeably herein.

As used herein, the term "host" refers to an animal, e.g., a mammal such as a rodent (e.g., mouse), non-human primate (e.g., monkey), human, or agriculturally important livestock such as cattle, swine, or poultry, that can be infected by an infectious organism described herein.

As used herein, an "immune response" refers to the concerted action of lymphocytes, antigen presenting cells, phagocytic cells, and various soluble macromolecules in defending the body against infection.

The details of one or more embodiments of the invention are set forth in the accompanying drawings and the description below. Other features, objects, and advantages of the invention will be apparent from the description and drawings, and from the claims.

DETAILED DESCRIPTION

*Vibrio cholerae* Strains

Figure 1A:
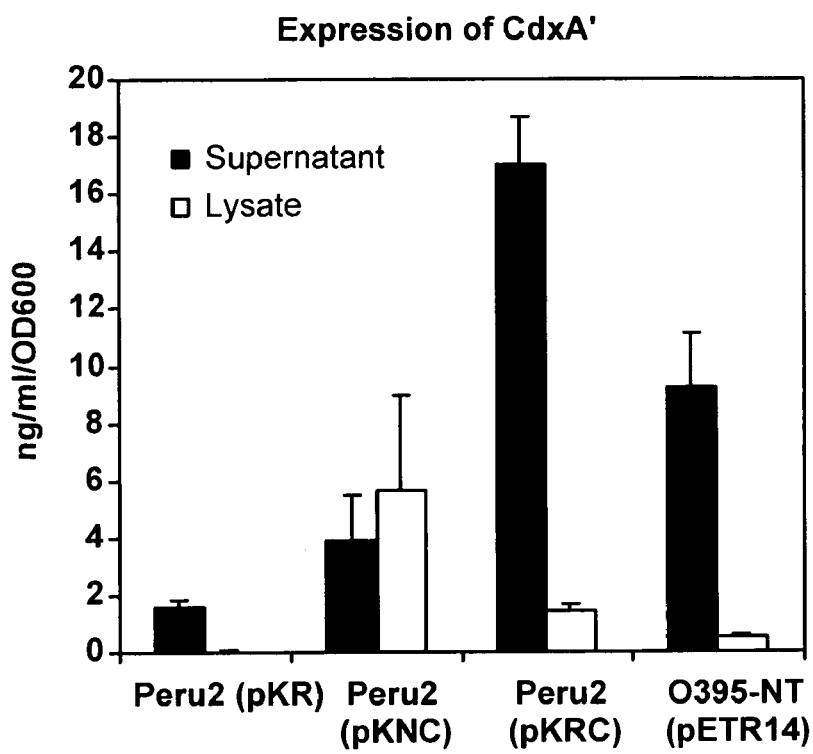
FIG. 1A is a graph of the expression of CdxA in the supernatants and cell lysates following introduction of various plasmids.

*V. cholerae* strains useful in the compositions and methods described herein are strains that endogenously express and secrete the protein RTX ("repeats-in-toxin"). 0139 and El Tor strains of *V. cholerae* express and secrete RTX, which causes cell rounding in the infected animal and increased permeability through paracellular tight junctions due to covalent cross-linking of actin monomers leading to depolymerization of actin stress fibers (see, e.g., Fullner et al., EMBO J. 19:5315–5323, 2000; Fullner et al., Infect. Immun. 69:6310–6317, 2001). RTX is part of an operon system that has similarities to the type I hemolysin secretion system of *E. coli*.

RTX-expressing *V. cholerae* strains that can be used in the compositions and methods described herein are described, e.g., by Lin et al., Proc. Natl. Acad. Sci. USA 96:1071–1076, 1999, and include, e.g., 0139 strains and the El Tor strains N16961, KFV42, P27459, E7946 and C6709. Derivatives, e.g., attenuated derivatives, of such strains can also be used in the compositions and methods described herein. An attenuated derivative of a *V. cholerae* strain can be produced by introducing a modification, e.g., a deletion or mutation, of a gene, resulting in reduced or no toxicity. An attenuated strain can be, e.g., a derivative of the C6709 strain, e.g., Peru2. Preferably, the natural ctxA locus on the *V. cholera* chromosome is deleted or otherwise inactivated, so that biologically active cholera toxin cannot be expressed from the chromosome. For example, the ctxA deletion can be identical to that of strain 0395-N1 (Mekalanos, U.S. Pat. No. 4,882,278). Such deletions, mutations and insertions can readily be carried out by one of ordinary skill using the methods described herein, or other well-known, standard techniques. See, e.g., Sambrook et al., Molecular Cloning: A Laboratory Manual, 3d Ed., Cold Spring Harbor Laboratory Press 2001); Drinkwater and Klinedinst Proc. Natl. Acad. Sci. USA 83:3402–3406 (1986); Liao and Wise, Gene 88:107–111 (1990); Horwitz et al., Genome 3:112–117 (1989). The *V. cholerae* strains described herein are useful for expressing and secreting fusion proteins containing a heterologous antigen and all or a portion of an RTX protein.

Heterologous Polypeptides

"Heterologous polypeptide", as used herein, is a polypeptide that is not naturally expressed by *V. cholerae*. For example, a heterologous polypeptide can be a protein (or portion thereof) that is naturally expressed by an infectious organism other than *V. cholerae*. The heterologous polypeptide can be, e.g., a heterologous antigen. "Heterologous antigen", as used herein, is a polypeptide that is immunogenic, i.e., induces an antigenic response in an animal, e.g., a mammal, e.g., a human, non-human primate, cow, horse, sheep, goat, pig, dog, cat, rabbit, rat, mouse, guinea pig or hamster.

The infectious organism can be, e.g., a bacterium (e.g., *Clostridium difficile* or *E. coli*), a virus, or a eukaryotic parasite. Preferred heterologous polypeptides, e.g., heterologous antigens, include, e.g., an immunogenic bacterial toxin such as *C. difficile* toxin A, Shiga toxin, diphtheria toxin, *Pseudomonas* exotoxin A, pertussis toxin, tetanus toxin, anthrax toxin, one of the *E. coli* heat-labile toxins (LTs), one of the *E. coli* heat-stable toxins (STs), or one of the *E. coli* Shiga-like toxins; an OSP (Outer Surface Protein) of *Borelia burgdorferai*; an immunogenic, nontoxic bacterial protein such as a colonization factor of diarrheogenic *E. coli*, a colonization factor of *Bordetella pertussis*, a pilin of uropathogenic *E. coli*, or a pilin of *Neisseria gonorrhoeae*; an immunogenic viral surface protein from a virus such as human immunodeficiency virus (HIV), Herpes virus (e.g., Herpes simplex virus or Epstein-Barr virus), influenza virus, poliomyelitis virus, measles virus, mumps virus, rubella virus, rotavirus, respiratory syncytial virus, adenovirus, or papilloma virus; or an immunogenic protein derived from a eukaryotic parasite, such as the causative agent for malaria, pneumocystis pneumonia, or toxoplasmosis. One example of such a polypeptide is a malarial circumsporozoite protein.

Preferably, the heterologous polypeptide, e.g., heterologous antigen, is derived from *Clostridium difficile*. *C. difficile* is the causative agent of pseudomembranous colitis and results in significant morbidity, mortality, and cost (Kelly et al., Gastroenterology, 1992, 102:35–40; Lyerly et al., Clin. Microbiol., 1988, Rev. 1:1–18; Mitty et al., Gastroenterologist, 1994, 2:61–69). *C. difficile* causes pseudomembranous colitis through the action of two large toxins, toxin A and toxin B, that modify Rho proteins with subsequent disruption of the actin cytoskeleton (Dillon et al., Infect. Immun., 1995, 63:1421–1426). Toxin A appears to initiate intestinal damage, to produce mucosal disruption, and to permit full cytotoxicity of toxin B (Lyerly et al., Clin. Microbiol., 1988, 1:1–18). The gene encoding toxin A has been sequenced (Dove et al., 1990, Infect. and Immun. 58:480–488, and von Esc et al., 1990, Gene 96:107–113). The carboxyl-third of toxin A, which is approximately 800 amino acids in length, is essential for toxin binding to trisaccharide receptors on human intestinal epithelial cells (Dove et al., 1990, Infect. and Immun. 58:480–488; Krivan et al., Infect. Immun., 1986, 53:573–581; Lyerly et al., Clin. Microbiol., 1988, 1:1–18; Sauerborn et al., Nucl. Acids Res., 1990, 18:1629–1630; Tucker et al., Infect. Immun., 1991, 59:73–78; von Eichel-Streiber et al., Gene, 1990, 96:107–113). Antibodies directed against toxin A prevent toxin binding, neutralize secretory and inflammatory effects, and limit or prevent clinical disease (Allo et al., Gastroenterology, 1979,76:351–355; Corthier et al., Infect. Immun., 1991, 59:1192–1195; Johnson et al., J. Immunol., 1993, 150:117A Abstract #657; Ketley et al., J. Med. Microbiol., 1987, 24:41–52; Kim et al., Infect. Immun., 1987, 55:2984–2992; Leung et al., J. Pediatr., 1991, 118:633–637; Warny et al., Infect. Immun., 1994, 62:384–389). Antibodies specifically directed against the carboxyl terminus of toxin A have been shown to prevent holotoxin binding and abrogate subsequent cytotoxic events (Corthier et al., Infect. Immun., 1991, 59:1192–1195; Frey et al., Infect. Immun., 1992, 60:2488–2492; Lyerly et al., Clin. Microbiol., 1988, Rev. 1:1–18; Wren et al., Infect. Immun., 1991, 59:3151–3155).

Fusion Proteins of Heterologous Polypeptides and RTX

The compositions described herein include fusion proteins that include a heterologous polypeptide, e.g., a heterologous antigen, and an RTX protein, or portion thereof, provided that the portion of the RTX protein, when joined to the heterologous polypeptide, retains the ability to direct secretion of the fusion protein. Fusion proteins comprising various portions of an RTX protein rather than a complete RTX protein can be produced by routine methods such as those described hereinafter or in molecular biology and biochemistry textbooks (e.g., Sambrook et al., Molecular Cloning: A Laboratory Manual, 3d Ed., Cold Spring Harbor Laboratory Press 2001); Deutscher, M., Guide to Protein Purification Methods Enzymology, vol. 182, Academic Press, Inc., San Diego, Calif. (1990)). The level of secretion of fusion proteins containing a particular portion of an RTX protein can be tested using methods described herein. Minimally, the portion will include the secretory signal sequence located at the carboxyl terminus of the RTX protein (see, e.g., Fullner et al., Proc. Natl. Acad. Sci. USA 96:1071–1076, 1999).

Nucleic acid sequences encoding a fusion protein described herein can be synthesized chemically or by recombinant means. For example, a nucleic acid encoding a heterologous polypeptide can be joined to one end of a nucleic acid sequence encoding the RTX protein or portion thereof such that the two protein-coding sequences share a common translational reading frame and can be expressed as a fusion protein including the heterologous polypeptide and the RTX protein. The combined sequence is inserted into a suitable vector chosen based on the expression features desired. In the examples provided hereinafter, the nucleic acid sequences are assembled in a vector suitable for protein expression in *V. cholerae* cells.

Frequently used specific expression units including promoter and 3' sequences are those found in plasmid pBR322 (Pharmacia), plasmid c CDNA3 (Invitrogen), plasmid AH5, pRC/CMV (Invitrogen), pCMU II (Paabo et al., *EMBO J.* 5:1921–1927 (1986)), pZip-Neo SV (Cepko et al., *Cell* 37:1053–1062 (1984)) and pSRa (DNAX, Palo Alto, Calif.). The introduction of genes into expression units and/or vectors can be accomplished using routine genetic engineering techniques, as described in manuals like Molecular Cloning: A Laboratory Manual, 3d edition. (Sambrook, Fritsch and Maniatis, eds.), Cold Spring Harbor Laboratory Press, 2001; DNA Cloning, Volumes 1 and 11 (D. N. Glover, ed), 1985; Oligonucleotide Synthesis, (M. J. Gait, ed.), 1984; U.S. Pat. No. 4,683,195 (Mullis et al.,); Nucleic Acid Hybridization (B. D. Harries and S. J. Higgins, eds.), 1984; Transcription and Translation (B. D. Harries and S. J. Higgins, eds.), 1984; Culture of Animal Cells (R. I. Freshney, ed). Alan R. Liss, Inc., 1987; Immobilized Cells and Enzymes, IRL Press, 1986; A Practical Guide to Molecular Cloning (B. Perbal), 1984; Methods in Enzymology, Volumes 154 and 155 (Wu et al., eds), Academic Press, New York; Gene Transfer Vectors for Mammalian Cells (J. H. Miller and M. P. Calos, eds.), 1987, Cold Spring Harbor Laboratory; Immunochemical Methods in Cell and Molecular Biology (Mayer and Walker, eds.), Academic Press, London, 1987; Handbook of Experiment Immunology, Volumes I–IV (D. M. Weir and C. C. Blackwell, eds.), 1986; Manipulating the Mouse Embryo, Cold Spring Harbor Laboratory Press, 1986.

A nucleic acid encoding a fusion protein described herein can be expressed in *V. cholerae* cells by integrating the nucleic acid into the *V. cholerae* genome or by inserting the nucleic acid into an expression vector or plasmid that is introduced into a *V. cholerae* cell. A given *V. cholerae* cell can express one or more of these nucleic acids from a plasmid, or the nucleic acid can be integrated into the cell's chromosome. Conventional molecular biology techniques can be used to produce recombinant *V. cholerae* strains and plasmids for use in the compositions and methods described herein. Routine methods for introducing expression vectors into bacterial cells, e.g., electroporation, are known in the art. Methods for in vivo marker exchange, to introduce genes into the *V. cholerae* chromosome, are known to those of skill in the art (see, e.g., Butterton et al., 1995, Infect. Immun. 63:2689–2696).

Detection of Fusion Proteins

A variety of methods can be used to determine the level of expression of a fusion protein by a cell, e.g., a *V. cholerae* cell. In general, these methods include contacting an agent that selectively binds to the protein, such as an antibody, with a cell, culture medium, or cell lysate, to evaluate the level of the protein in the cell, medium, or lysate. In a preferred embodiment, the antibody bears a detectable label. Antibodies can be polyclonal, or more preferably, monoclonal. An intact antibody, or a fragment thereof (e.g., Fab or F(ab')$_2$), can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance.

In vitro techniques for detecting expression of a fusion protein include, e.g., enzyme linked immunosorbent assays (ELISAs), immunoprecipitations, immunofluorescence, enzyme immunoassay (EIA), radioimmunoassay (RIA), and Western blot analysis. For example, *V. cholerae* cells can be maintained in culture and the level of a fusion protein secreted into the culture medium can be determined by a method described herein. The methods can also include lysing the *V. cholerae* cells and detecting the level of fusion protein in the cell lysate.

Isolation and Purification of Heterologous Polypeptides

The methods and compositions described herein can be used in the production and isolation of heterologous polypeptides. A fusion protein described herein can be recovered and purified from a *V. cholerae* cell culture by well-known methods. For example, following the growth of the *V. cholerae* cells and concomitant secretion of the fusion protein into the culture medium, the medium is harvested. The medium is then clarified by, e.g., centrifugation or filtration to remove cells and cell debris. Further purification of the fusion proteins can be accomplished in the manner described in Galvin et al. (1987) J. Biol. Chem. 262: 2199–2205 and Salem et al. (1984) J. Biol. Chem. 259: 12246–12251. The purification of fusion proteins may require the additional use of, e.g., affinity chromatography, conventional ion exchange chromatography, sizing chromatography, hydrophobic interaction chromatography, reverse phase chromatography, gel filtration or other conventional protein purification techniques. See, e.g., Deutscher, ed. (1990) "Guide to Protein Purification" in Methods in Enzymology, Vol. 182.

A heterologous polypeptide described herein can be further isolated from a fusion protein using, e.g., a protease to cleave the RTX protein or portion thereof. For example, a nucleic acid encoding a unique protease cleavage site can be inserted between the nucleic acid encoding the heterologous polypeptide and the nucleic acid sequence encoding the RTX protein or portion thereof. Following purification, the fusion protein can be treated with the protease and the heterologous polypeptide isolated from the RTX protein or portion thereof using methods known in the art, such as those described herein.

Induction of Immune Responses

*V. cholerae* cells described herein are also useful to induce an immune response in an animal. For example, the cells can be combined with a pharmaceutically acceptable excipient suitable for oral administration to form a therapeutic composition, e.g., vaccine. Administration of such a therapeutic composition, e.g., vaccine, to an animal (e.g., a human or other mammal) can provoke immunity not only to *V. cholerae*, but also to the organism from which the heterologous polypeptide, e.g., heterologous antigen, is derived. An exemplary therapeutic composition utilizes a *V. cholerae* strain genetically engineered to express a fusion protein that includes (a) an antigenic, non-toxic portion of *C. difficile* toxin A and (b) a fragment of a *V. cholerae* RTX protein that includes the secretion signal sequence of the RTX protein. This strain is described in detail below. A *V. cholerae* strain described herein can also be engineered to encode several heterologous polypeptides, e.g., heterologous antigens, each linked to an identical or different promoter, to produce a multivalent therapeutic composition, e.g., vaccine, effective for simultaneously inducing immunity against a number of antigens or infectious organisms. In such strains, the various heterologous antigens can form part of one or more fusion proteins (e.g., fused with RTX or a secretion-promoting portion thereof) that are expressed in the *V. cholerae* cells.

The immune system is thought to be functionally separated into systemic and mucosal immune compartments (Czerkinsky et al., Cellular and Molecular, 1994, 1:3744). The mucosal immune system represents the largest immunological organ in the body. Luminal antigens are processed via M (microfold) cells, which are specialized epithelial cells found in the gastrointestinal tract and are involved in the induction of a mucosal immune response (Neutra et al., Johnson L R, ed. Physiology of the Gastrointestinal Tract, Third Edition, 1994, 685–708). Antigen processing and presentation are followed by proliferation and differentiation of IgA-committed, antigen-specific B lymphocytes that circulate via the bloodstream and populate the lamina propria of the upper respiratory, intestinal, and genitourinary tracts, as well as the salivary and mammary glands. In these effector sites, plasma cells produce antigen-specific IgA, which is then secreted across epithelial cells, acquiring secretory component in the process (Neutra et al., Johnson L R, ed., Physiology of the Gastrointestinal Tract, Third Edition, 1994, 685–708). Secretory component enhances resistance of these antibodies to proteolysis. The circulation of antigen-specific cells from one inductive site to multiple effector sites has led to the concept of a common mucosal immune system.

The compositions and methods described herein offer several advantages. *V. cholera* is a non-invasive organism that attaches selectively to intestinal M cells. In one embodiment, heterologous polypeptides, e.g., heterologous antigens, can be presented directly to underlying lymphoid tissues, permitting strong and long-lasting mucosal immune responses. *V. cholerae* colonizes human intestinal tissues for 7–14 days, thereby allowing for repeated antigenic presentation after a single administration of the therapeutic composition, e.g., vaccine.

The therapeutic compositions described herein can be administered to a subject in a variety of ways. The routes of administration can include, e.g., oral, and intranasal routes. Any other convenient route of administration can be used, for example, infusion or bolus injection, or absorption through epithelial or mucocutaneous linings. In addition, the compositions described herein can contain and be administered together with other pharmacologically acceptable components such as biologically active agents (e.g., adjuvants such as alum), surfactants (e.g., glycerides), excipients (e.g., lactose), carriers, diluents and vehicles.

EXAMPLES

Example 1

Secretion of a *C. difficile* Toxin A-RTX Fusion Protein by *V. cholerae*

Bacterial Strains and Expression Plasmids

*V. cholerae* strains and plasmids used in this study are described in Table 1. All strains were maintained at −70° C. in Luria-Bertani (LB) broth medium containing 15% glycerol. Streptomycin (100 µg/ml) and ampicillin (100 µg/ml) were added as appropriate. Cultures were grown at 37° C. with aeration.

TABLE 1

| | Bacterial strains and plasmids | |
|---|---|---|
| Strain or Plasmid | Relevant genotype or phenotype | Source or reference |
| *V. cholerae* strains | | |
| O395-NT | O1, classical, Ogawa, Δ ctxAB, Km$^r$, Sm$^r$ | a |
| C6709 | O1, El Tor, Inaba, wild-type; Sm$^r$ | b, c |
| Peru2 | C6709 Δ attRS1; Sm$^r$ | b, c |

TABLE 1-continued

Bacterial strains and plasmids

| Strain or Plasmid | Relevant genotype or phenotype | Source or reference |
|---|---|---|
| E. coli strains | | |
| JM105 | Thi, rpsL, endA, sbcB15, hsdR4, supE, Δ(lac-proAB), F' [traD36, proAB+, lacIq, lacZ ΔM15]; Smr | d |
| Plasmids | | |
| pKK223-3 | pBR322-based plasmid containing a multiple cloning site (MCS) between the tac promoter and the rrnB transcriptional terminator; Ampr | d |
| pKR | pKK223-3 derived plasmid containing a 450 bp fragment encoding the 50 amino acid N-terminal sequence fused with 100 amino acid C-terminal secretion signal of RTX of C6709, containing a unique NsiI site within RTX'; Ampr | e |
| pKRC | Derived from pKR, containing a 900 bp PstI fragment encoding the nontoxic carboxyl-terminal of C. difficile toxin A (CdxA), inserted in the NsiI site of the truncated RTX; Ampr | e |
| pKNC | Derived from pKK223-3, containing a PCR amplified fragment encoding a 150 bp of the N-terminal part of RTX and a 900 bp CdxA, inserted into the MCS of pKK223-3; Ampr | e |
| pMOhly1 | Plasmid encoding the hemolysin operon of E. coli, with internal deletion of hlyA such that nucleotides for the amino terminal 34 amino acids are fused with nucleotides for the carboxyl terminal 61 amino acid HlyA secretion signal, containing a unique NsiI site without hlyA'; Ampr | f |
| pETR14 | Derived from pMOhly1 containing a 2100 bp PstI fragment encoding the nontoxic caraboxyl-terminal of C. difficile Toxin A, inserted in the NsiI site; Ampr | g |
| pET41 | Derived from pBR322, containing T7lac promoter controlling expression of a 220 amino acid GST tag; Knr | h |
| pKRG | Derived from pKR with insertion of a 600 bp NsiI fragment encoding GST' amplified from pET41; Ampr | e |

Ampr, ampicillin resistant;
Smr, streptomycin resistant;
Knr, kanamycin resistant
a. Mekalanos et al., Nature 306:551–557, 1983
b. Taylor et al., J. Infect. Dis. 170:1518–1523, 1994
c. Butterton et al., Infect. Immun. 63:2689–2696, 1995
d. Pharmacia P-L Bio-chemical Inc., Milwaukee, WI
e. Described herein
f. Gentschev et al., Infect. Immun. 63:4202–4205, 1995
g. U.S. Pat. No. 6,036,953
h. Novagen, EMD Biosciences Inc., Germany Molecular Biology and Transformation Isolation of plasmid DNA, restriction enzyme digestion, and agarose gel electrophoresis were performed by standard molecular biological techniques. Plasmids were electroporated into V. cholerae with a Gene Pulser (Bio-Rad Laboratories, Richmond, Calif.) as instructed by the manufacturer and modified for electroporation into V. cholerae as described previously (Goldberg et al., Proc. Natl. Acad. Sci. USA, 1991, 88:1125–1129). Electroporation conditions were 2,500 V at 25 μF capacitance, producing time constants of 4.8 to 4.9 ms.

In Vitro Analysis of Heterologous Antigen Expression

In vitro expression of C. difficile toxin A (CdxA) derivatives (either CdxA'-RTX' or CdxA'-HlyA') was analyzed with the V. cholerae El Tor vaccine strain Peru2 and the V. cholerae classical strain O395-NT. One microliter of overnight culture was centrifuged at 7,000 rpm for 15 min; supernatant fractions were recovered, and pellets were resuspended in 0.1 ml of lysozyme in Tris buffer (pH 8.0, 1 μg/ml). Resuspended pellets were incubated at 37° C. for 1 hr, adjusted to original volume by adding 0.9 ml of LB broth, and subject to repeated freezing-thawing at 37° C. and −20° C. Lysates were recovered by centrifuging at 13,200 rpm for 10 min. Supernatant and lysate samples were analyzed in an enzyme-linked immunosorbent assay (ELISA) for CdxA. Six individual samples of each construct were applied to 96-well microtiter plates previously coated with 1.5 μg of rabbit anti-CdxA (Lee Laboratories Inc. GA) in PBS buffer (pH 7.4) per well. Plates were incubated at 37° C. for 1 hr. Plates were analyzed with goat anti-CdxA (1:2000, Techlab), followed by rabbit anti-goat IgG-horse radish peroxidase (HRP) conjugates (1:2000). Plates were developed with a solution containing 2,29-azinobis(3-ethylbenz-thiazolinesulfonic acid) (ABTS) (Sigma) at concentration of 1 μg/ml and 0.1% $H_2O_2$ (Sigma), and the optical density at 405 nm was determined kinetically with a Vmax microplate reader (Molecular Devices Corp., Sunnyvale, Calif.). Plates were read for 5 min at 22-sec intervals, and the maximum slope for an optical density change of 0.2 U was reported as milli-optical density units per minute. Concentrations were calculated using to a standard curve generated by a purified CdxA (Tech Lab. Inc, Va.).

As shown in FIG. 1A, the transformation of Peru2 cells with pKRC (containing a 900 bp fragment encoding the nontoxic carboxyl-terminal of C. difficile toxin A (CdxA) inserted between the 50 amino acid N-terminal sequence and the 100 amino acid C-terminal secretion signal of RTX of C6709) resulted in secretion of the fusion protein into the supernatant. This was markedly better than the pKNC plasmid (lacking the RTX secretion signal sequence) and better than introduction of pETR14 (encoding the HlyA secretion system) into O395-NT. This demonstrates that the endogenous RTX secretion system present in V. cholerae can be used to express and secrete large heterologous polypeptides.

Figure 1B:
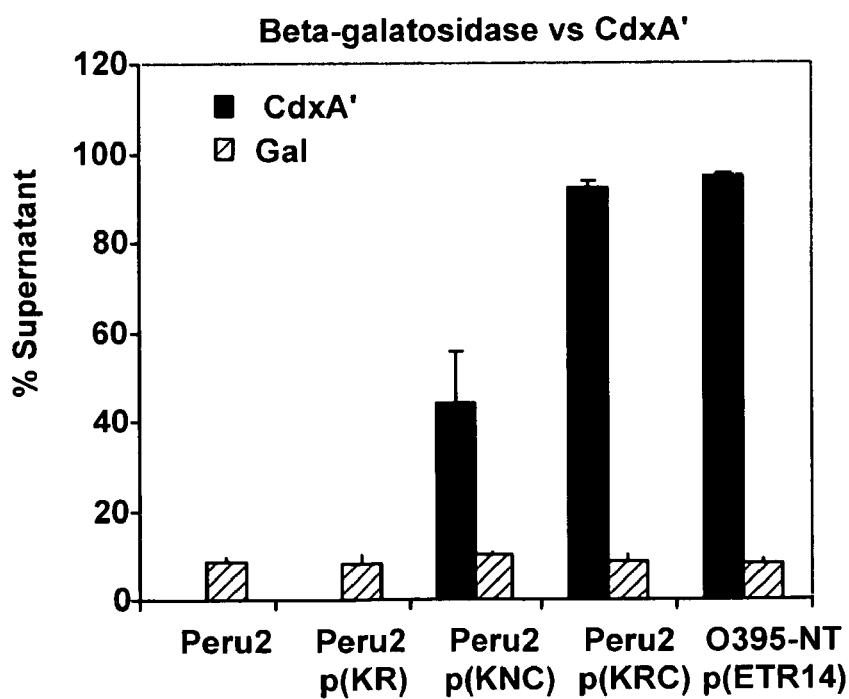
FIG. 1B is a graph of the expression of CdxA and beta galactosidase in the supernatants and cell lysates following introduction of various plasmids.

To determine whether the expression and secretion of the fusion protein encoded by pKRC was due to nonspecific cell lysis, endogeneous beta-galactosidase activity of V. cholerae was chosen as a cytoplasmic marker to assess cell lysis. Beta-galactosidase activities were measured as previously described (see, e.g., U.S. Pat. No. 6,036,953). Supernatants were prepared as described above. One hundred microliters of an overnight culture or its supernatant was added to 900 μl of Z buffer (60 mM $Na_2HPO_4$, 40 mM $NaH_2PO_4$, 10 mM KCl, 1 mM $MgSO_4$, 50 mM beta-mercaptoethanol, pH 7.0). Five microliters of 20% SDS were added. Samples were vortexed and incubated at 37° C. for 30 min. 0.2 ml of o-nicrophenyl-β-D-galactopyranoside (4 mg/ml; Sigma) in 0.1 M sodium phosphate buffer (pH 7.0) was added, and samples were re-incubated at 37° C. until yellow. Reactions were stopped with 0.2 ml of 1 M sodium carbonate. Adsorbances at 420 and 550 nm were read. The percentage of beta-galactosidase in the supernatant was compared to the percentage of CdxA' in supernatant measured in parallel. As shown in FIG. 1B, the percentage of CdxA' in supernatant was greater than the percentage of beta-galactosidase in supernatant. This demonstrates that the secretion of the RTX-heterologous polypeptide fusion protein seen in FIG. 1A was not due to nonspecific cell lysis.

Figure 2A:
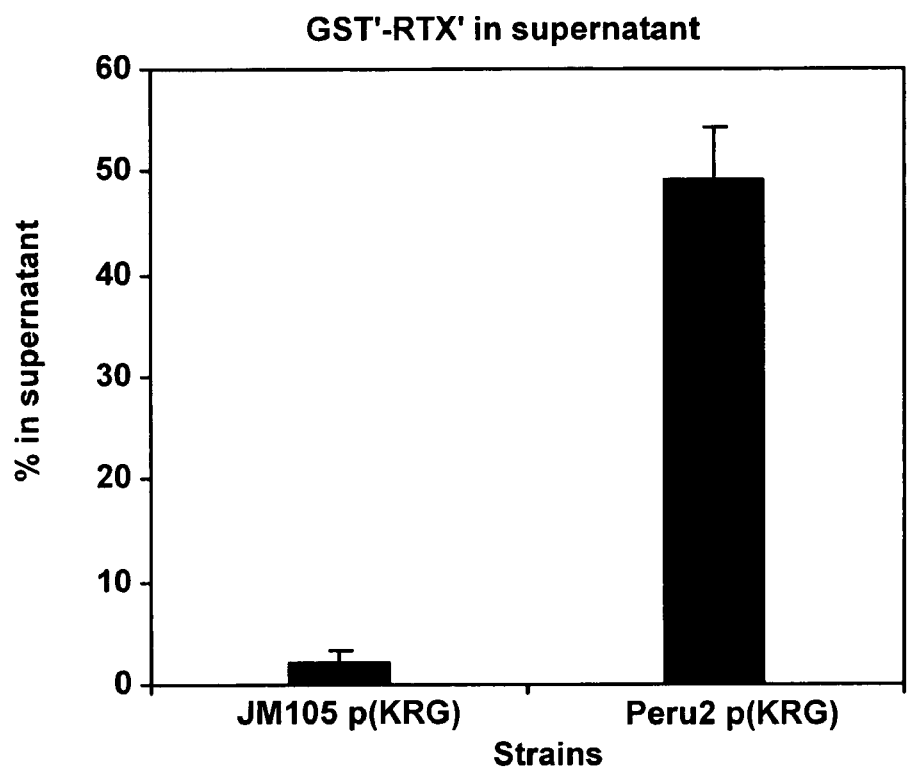
FIG. 2A is a graph of the expression of a GST-RTX fusion protein in the supernatants of two *V. cholerae* strains.
Figure 2B:
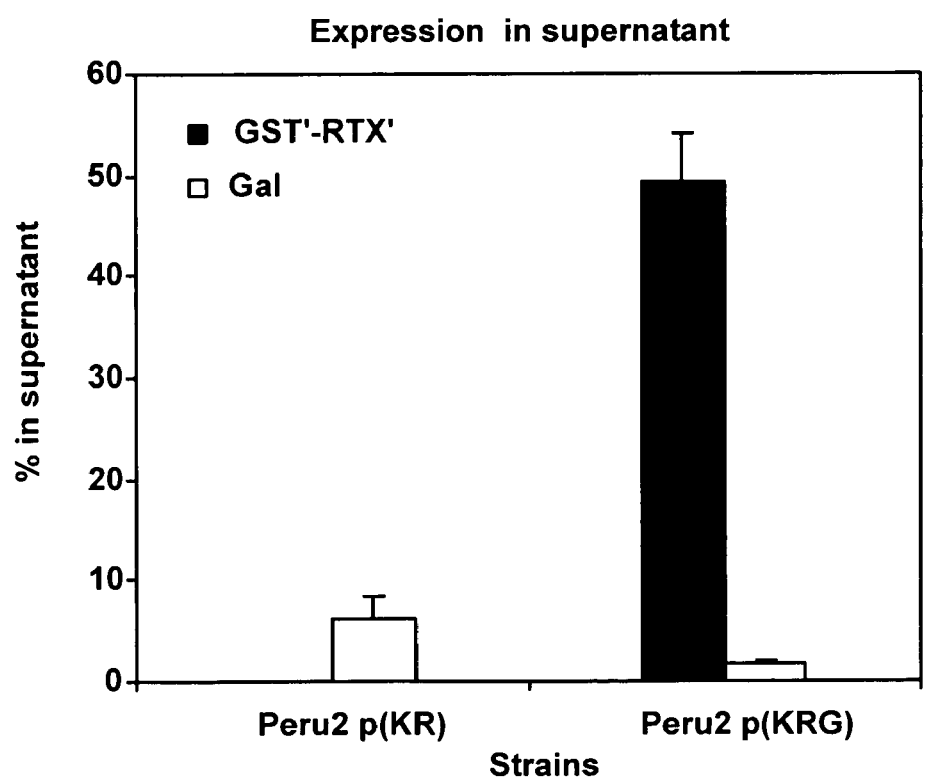
FIG. 2B is a graph of the expression of a GST-RTX fusion protein and of beta galactosidase in the supernatants of two *V. cholerae* strains.

To demonstrate that secretion of an RTX fusion protein could be obtained by using the endogenous RTX secretion system of *V. cholerae* cells, the in vitro expression of a GST'-RTX' fusion protein was analyzed in *E. coli* JM105 cells and *V. cholerae* Peru2 cells. One microliter of overnight culture was treated as mentioned above, with additional induction of expression of GST'-RTX' in *E. coli* by 1 mM IPTG, at room temperature for 1 hr. Supernatant and lysate samples were analyzed in an ELISA assay for GST. Six individual samples of each construct were applied to 96-well microtiter plates previously coated with 1.5 mg of mouse monoclonal anti-GST antibodies (Novagen, EMD Biosciences Inc., Germany) in PBS buffer (pH 7.4) per well. Plates were incubated at 37° C. for 1 hr. Plates were analyzed with goat anti-GST (1:2000, Amersham Biosciences, N.J.), followed by rabbit anti-goat IgG-horse radish peroxidase (HRP) conjugates (1:2000). Plates were developed by ABTS as mentioned as above. Concentrations were calculated using to a standard curve generated by a purified GST (Novagen). As seen in FIG. 2A, GST'-RTX' was secreted into the supernatant by the *V. cholerae* Peru2 cells, but not by the *E. coli* cells. FIG. 2B demonstrates that the secretion of the GST'-RTX' fusion protein by *V. cholerae* Peru2 cells was specific, because beta galactosidase was not detected in the supernatant.

Example 2

Induction of an Immune Response Using a *V. cholerae* Cell Expressing a *C. difficile* Toxin A-RTX Fusion Protein Inoculation and Colonization of Germfree Mice Immediately upon removal of mice from their germfree shipping carton, 4 groups of 6 to 10 germfree female Swiss mice, 3 to 4 weeks old (Taconic Farms, Inc., Germantown, N.Y.) were orally inoculated with 120 μl inocula containing approximately $10^9$ organisms of *V. cholerae* vaccine strains resuspended in 0.5 M $NaHCO_3$ (pH 8.0) supplemented with 5% sucrose. Groups of 6 to 10 mice each received inoculations of Peru2(pKRC), Peru2(pKNC), Peru2(pKR) or O395-NT(pETR14). Mice were subsequently housed in nongermfree condition. Oral inoculations were given at day 0, 2, 4, 6, 14, 28, 42, 56 and 84. Intra-nasal inoculations were given with 15 μl inocula containing approximately $10^9$ organisms of *V. cholerae* strains resuspended in PBS supplemented with 5 μg of purified cholera toxin (CT; List Biological Laboratories, Inc., Campbell, Calif.) as immunoadjuvant. Intra-nasal inoculations were given at day 85, 91, 98, 105, 112, 133 and 147.

To ascertain the presence of plasmids, fresh stool samples were collected immediately upon passage from mice until day 4 after oral inoculation, resuspended in 500 μl of LB broth, vortexed, and allowed to settle. One hundred microliter aliquots were plated on LB agar medium containing ampicillin, and colonies were subsequently confirmed as *V. cholerae* on thiosulfate-citrate-bile salts-sucrose medium. Plasmid preparations from randomly selected, ampicillin-resistant colonies from stool samples collected 72 hr after oral inoculation were examined to evaluate presence of vaccine strains.

Immunological Sampling

Mice were sacrificed on day 154, at which time blood was collected via intra-cardiac puncture. Blood was allowed to clot, and serum was separated by centrifugation. Bile (10 to 20 μl) was collected via hepatic dissection and subsequent aspiration of the gallbladder. Fresh stool pellets were collected for immunological evaluation and stored at −70° C. until processed. Each pellet was then placed in 1 ml of a 3:1 mixture of PBS and vortexed until broken. The mixture was centrifuged twice. Stool, bile, and serum samples were divided into aliquots and stored at −70° C. for subsequent analysis.

Measurement of Systemic and Mucosal Anti-CdxA' and CT Antibody Responses

To detect anti-CdxA' antibody responses, microtiter plates were coated with 100 ng of CdxA or CT in PBS per well. Following overnight incubation at room temperature and three washes in PBS-T, the plates were blocked with 1% bovine serum albumin (BSA; Sigma). One hundred microliters of duplicate samples of 1:400 (for IgG) and 1:200 (for IgA) dilutions of sera in PBS-T were placed in wells of microtiter plates previously coated with CdxA or CT. Plates were incubated at 37° C. for 1 hr and washed in PBS-T (PBS with 0.05% Tween 20). A 1:2000 dilution in PBS-T of goat anti-mouse IgG conjugated to biotin or goat anti-mouse IgA conjugated to biotin (Kirkegaard & Perry Laboratories, Gaithersburg, Md.) was applied to each well, and the plates were again incubated at 37° C. for 1 hr. After plates were washed in PBS-T, a 1:2000 dilution of streptavidin-horseradish peroxidase conjugate (Zymed Laboratories, Inc., South San Francisco, Calif.) was added to each well, and plates were incubated at 37° C. for 1 hr. After being washed in PBS-T, plates were developed by ABTS as described above.

To detect specific IgA antibody responses in stool and bile, measurements of total stool and bile IgA were first taken. Duplicate of stool at 1:50 and bile at 1:100 samples in PBS-T were added to wells previously coated with 100 ng of rat monoclonal anti-mouse IgA antibody R5–140 (PharMingen, San Diego, Calif.) and previously blocked with PBS-BSA. Samples were incubated at 37° C. for 1 h and then washed with PBS-T. A 1:2000 goat anti-mouse IgA-horseradish peroxidase conjugate (Southern Biotechnology Associates, Birmingham, Ala.) in PBS-T was added to each well. After 1 h of incubation at 37° C., plates were washed with PBS-T and developed for horseradish peroxidase activity as described above. Comparisons were made to a mouse IgA standard (Kappa TEPC 15; Sigma).

To detect specific anti-Cdx' or anti-CT IgA antibodies in stool and bile, single (bile) or duplicate (stool) samples of 100 ml of PBS-T containing 750 ng of total IgA (stool) or 125 ng of total IgA (bile) were added to wells previously coated with CdxA or CT. Plates were incubated at 37° C. for 1 hr. After the plates were washed with PBS-T, a 1:2000 dilution of goat anti-mouse IgA-biotin conjugate (Kirkegaard & Perry) in PBS-T was added. After overnight incubation at room temperature, the plates were developed for horseradish peroxidase activity, and the optical density at 405 nm was determined kinetically.

Figure 3A:
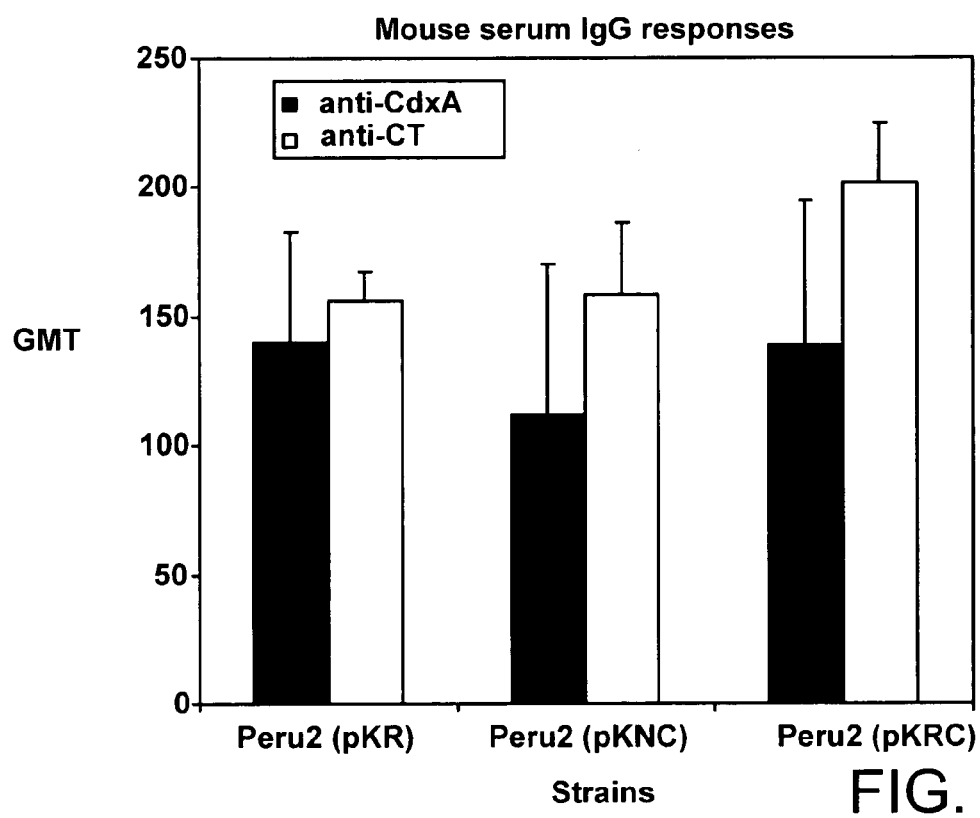
FIG. 3A is a graph of the level of mouse serum IgG following inoculation of mice with *V. cholerae* cells containing various plasmids.
Figure 3B:
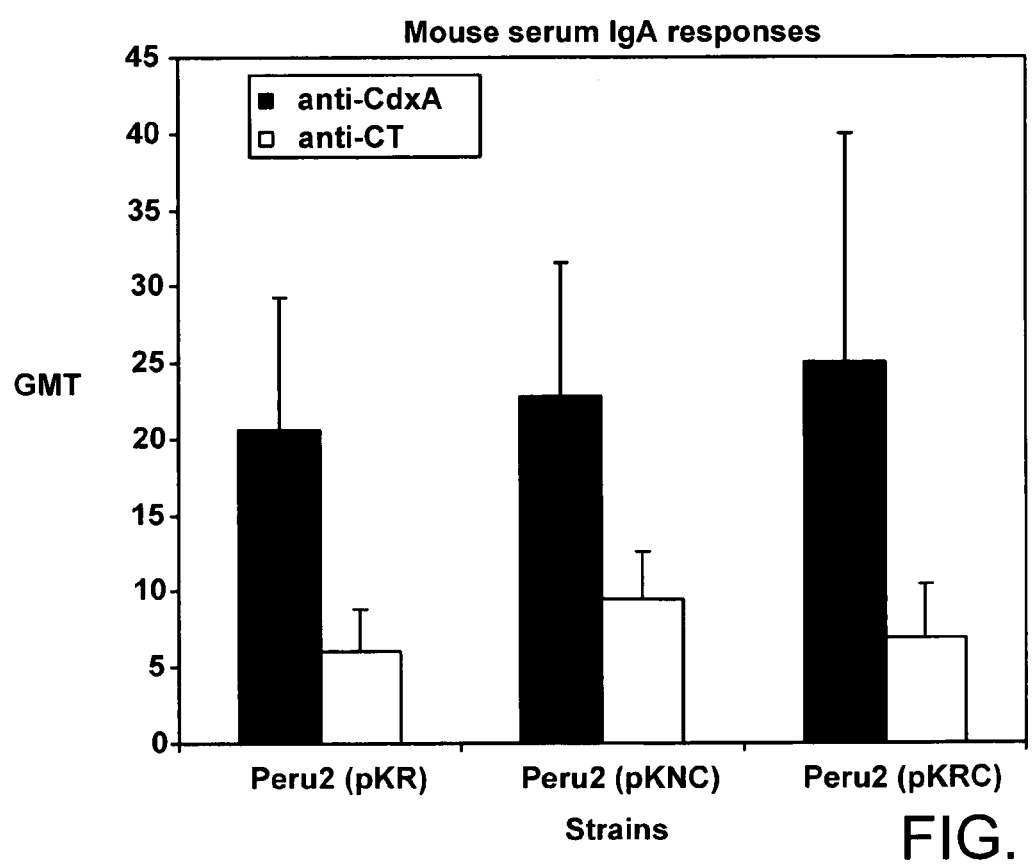
FIG. 3B is a graph of the level of mouse serum IgA following inoculation of mice with *V. cholerae* cells containing various plasmids.

As shown in FIG. 3A, there were no statistical differences in the anti-CdxA' IgG antibody levels in serum from mice inoculated with any of the *V. cholerae* strains. Inoculation with Peru2(pKR), which expresses a fusion protein that does not include CdxA', resulted in the same level of anti-Cdx' IgG antibodies as inoculation with Peru2(pKRC), which expresses a fusion protein containing the first 50 N-terminal amino acids of RTX, 300 amino acids of CdxA, and 100 C-terminal amino acids of RTX. Similar results were seen for mouse serum IgA responses (FIG. 3B). This result may reflect an artifact of the experiment, such as a toxicity of CdxA for immunological cells, and is not expected to be typical for heterologous antigens expressed via the RTX secretion system of the invention.

Statistics and Graphs

Statistical analysis for the comparison of geometric means was performed for normally distributed data with the independent-sample Student t test by SPSS12.0 for Windows 2000. Data were plotted with Microsoft Excel.

All publications and patents cited herein are hereby incorporated by reference. A number of embodiments of the invention have been described. Nevertheless, it will be understood that various modifications may be made without departing from the spirit and scope of the invention. Accordingly, other embodiments are within the scope of the following claims.

What is claimed is:

1. A nucleic acid encoding a fusion protein, wherein the fusion protein comprises:
    (a) a fragment of a *V. cholerae* RTX protein comprising the RTX secretion signal sequence; and
    (b) a heterologous polypeptide.
2. The nucleic acid of claim 1, wherein the fragment comprises at least 40 carboxyl terminal amino acids of the RTX protein.
3. The nucleic acid of claim 1, wherein the fragment comprises at least 100 carboxyl terminal amino acids of the RTX protein.
4. The nucleic acid of claim 1, wherein the fragment comprises at least 105 carboxyl terminal amino acids of the RTX protein.
5. The nucleic acid of claim 1, wherein the fragment consists of between 40 and 100 carboxyl terminal amino acids of the RTX protein.
6. The nucleic acid of claim 1, wherein the fragment consists of 100 carboxyl terminal amino acids of the RTX protein.
7. The nucleic acid of claim 1, wherein the fragment consists of 105 carboxyl terminal amino acids of the RTX protein.
8. The nucleic acid of claim 1, wherein the fusion protein further comprises an amino terminal fragment of the RTX protein.
9. The nucleic acid of claim 8, wherein the amino terminal fragment comprises 50 amino acids.
10. The nucleic acid of claim 9, wherein the amino terminal fragment consists of 50 amino acids.
11. The nucleic acid of claim 8, wherein the heterologous polypeptide is located between the amino terminal fragment and the fragment comprising the RTX secretion signal sequence.
12. The nucleic acid of claim 1, wherein the heterologous polypeptide is *C. difficile* toxin A.
13. The nucleic acid of claim 1, wherein the heterologous polypeptide comprises an antigenic portion of *C. difficile* toxin A.
14. The nucleic acid of claim 13, wherein the antigenic portion comprises a carboxyl terminal fragment of *C. difficile* toxin A.
15. The nucleic acid of claim 1, wherein the heterologous polypeptide comprises 300 carboxyl terminal amino acids of *C. difficile* toxin A.
16. An expression vector comprising the nucleic acid of claim 1.
17. A *V. cholerae* cell comprising the vector of claim 16.
18. A *V. cholerae* cell transfected with the vector of claim 16, wherein the cell expresses the fusion protein.
19. The *V. cholerae* cell of claim 18, wherein the cell secretes the fusion protein.
20. The *V. cholerae* cell of claim 18, wherein the *V. cholerae* cell is an El Tor *V. cholerae* cell.
21. The *V. cholerae* cell of claim 20, wherein the *V. cholerae* cell does not express cholera toxin A subunit.
22. The *V. cholerae* cell of claim 21, wherein the *V. cholerae* cell is a Peru2 *V. cholerae* cell.
23. A method for producing a fusion protein, the method comprising maintaining the cell of claim 17 under conditions sufficient to allow expression of the fusion protein.

* * * * *

UNITED STATES PATENT AND TRADEMARK OFFICE
CERTIFICATE OF CORRECTION

PATENT NO. : 7,049,423 B2
APPLICATION NO. : 11/018169
DATED : May 23, 2006
INVENTOR(S) : Edward T. Ryan Page 1 of 1

It is certified that error appears in the above-identified patent and that said Letters Patent is hereby corrected as shown below:

Add the following new paragraph at column 1, line 11:

--GOVERNMENT GRANT

This invention was made with Government support under Grant No. AI05725 awarded by the National Institutes of Health. The Government has certain rights in this invention.--

Signed and Sealed this

First Day of September, 2009

David J. Kappos
*Director of the United States Patent and Trademark Office*